US009133266B2

(12) United States Patent
Thomson et al.

(10) Patent No.: US 9,133,266 B2
(45) Date of Patent: Sep. 15, 2015

(54) VITRONECTIN-DERIVED CELL CULTURE SUBSTRATE AND USES THEREOF

(75) Inventors: James A. Thomson, Madison, WI (US); Zhonggang Hou, Madison, WI (US); Guokai Chen, Rockville, MD (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/464,235

(22) Filed: May 4, 2012

(65) Prior Publication Data

US 2012/0301962 A1 Nov. 29, 2012

Related U.S. Application Data

(60) Provisional application No. 61/483,521, filed on May 6, 2011.

(51) Int. Cl.
| | |
|---|---|
| *C12N 5/071* | (2010.01) |
| *C07K 14/78* | (2006.01) |
| *C12N 5/0735* | (2010.01) |
| *C12N 5/074* | (2010.01) |

(52) U.S. Cl.
CPC .............. *C07K 14/78* (2013.01); *C12N 5/0606* (2013.01); *C12N 5/0696* (2013.01); *C12N 2500/02* (2013.01); *C12N 2500/05* (2013.01); *C12N 2500/25* (2013.01); *C12N 2500/38* (2013.01); *C12N 2501/115* (2013.01); *C12N 2501/15* (2013.01); *C12N 2501/33* (2013.01); *C12N 2501/727* (2013.01); *C12N 2533/50* (2013.01); *C12N 2533/52* (2013.01)

(58) Field of Classification Search
None
See application file for complete search history.

(56) References Cited

U.S. PATENT DOCUMENTS

| 8,268,620 B2 | 9/2012 | Thomson et al. |
|---|---|---|
| 8,440,461 B2 | 5/2013 | Thomson et al. |
| 2006/0084168 A1* | 4/2006 | Thomson et al. ............. 435/366 |
| 2009/0047263 A1* | 2/2009 | Yamanaka et al. ......... 424/93.21 |

FOREIGN PATENT DOCUMENTS

WO WO 2004069871 A1 * 8/2004

OTHER PUBLICATIONS

Lewitzky et al. "Reprogramming somatic cells towards pluripotency by defined factors." Current Opinion in Biotechnology (2007); 18( 5): pp. 467-473.*
Niwa et al. "Quantitative expression of Oct-3/4 defines differentiation, dedifferentiation or self-renewal of ES cellsi." Nature Genetics (2000); 24: pp. 372-376.*
Yamanaka et al. "Induction of pluripotent stem cells from mouse fibroblasts by four transcription factors." Cell Proliferation (2008); 41 ( 51): pp. 51-56.*
Stadtfeld et al. "Induced Pluripotent Stem Cells Generated Without Viral Integration." Science (2008); 322 (5903): pp. 945-949.*
Okita et al. "Generation of mouse induced pluripotent stem cells without viral vectors." Science (2008); 322 (5903): pp. 949-953.*
Gonzalez et al. "Generation of mouse-induced pluripotent stem cells by transient expression of a single nonviral polycistronic vector." PNAS (2009); 106 (22): pp. 8918-8922.*
Braam et al. "Recombinant Vitronectin Is a Functionally Defined Substrate That Supports Human Embryonic Stem Cell Self-Renewal via alphaVBeta5 Integrin." Stem Cells ( 2008);26: pp. 2257-2265.*
Zhao et al. "The cell attachment and spreading activity of vitronectin is dependent on the ARG-GLY-ASP sequence: Analysis by construction of RGD and domain deletion mutants." Biochemical and Biophysical Research Communications (1993); 192 (2): pp. 575-582.*
Rowland et al. "Roles of Integrins in Human Induced Pluripotent Stem Cell Growth on Matrigel and Vitronectin." Stem Cells and Development ( Aug. 2010); 19 (8): pp. 1231-1240.*
Djuric and Ellis. "Epigenetics of induced pluripotency, the seven-headed dragon." Stem Cell Research & Therapy. (2010); 1(3): pp. 1-6.*
Takahashi et al. "Induction of Pluripotent Stem Cells from Mouse Embryonic and Adult Fibroblast Cultures by Defined Factors." Cell. (2008);126: pp. 663-676.*
Huangfu et al. "Induction of pluripotent stem cells by defined factors is greatly improved by small-molecule compounds." Nature Biotechnology. (2008);26: pp. 795-797.*
Huangfu et al. "Induction of pluripotent stem cells from primary human fibroblasts with only Oct4 and Sox2." Nature Biotechnology(2008); 26,pp. 1269-1275.*
Plath et al. "Progress in understanding reprogramming to the induced pluripotent state." Nature Reviews Genetics (Apr. 2011);12: pp. 253-265.*
Chen et al, "Actin-myosin contractility is responsible for the reduced viability of dissociated human embryonic stem cells." Cell Stem Cell 7:240-248 (2010).
Evans, et al. "Establishment in culture of pluripotential cells from mouse embryos" Nature 292:154-156 (1981).
Ludwig et al., "Feeder-independent culture of human embryonic stem cells" Nat. Methods 3:637-646 (2006).
Miyazaki et al., "Recombinant human laminin isoforms can support the undifferentiated growth of human embryonic stem cells." Biochem. Biophys. Res. Commun. 375:27-32 (2008).
Prowse et al., "Long term culture of human embryonic stem cells on recombinant vitronectin in ascorbate free media." Biomaterials 31:8281-8288 (2010).
Watanabe et al., "A ROCK inhibitor permits survival of dissociated human embryonic stem cells." Nature Biotechnology 25:681-686 (2007).
Wojciechowski et al., "Expression, production, and characterization of full-length vitronectin in *Escherichia coli*." Protein Expr. Purif. 36:131-138 (2004).
Yu et al., "Human induced pluripotent stem cells free of vector and transgene sequences." Science 324:797-801 (2009).
Yu et al., "Induced Pluripotent Stem Cell Lines Derived from Human Somatic Cells" Science (2007) vol. 318 (5858) pp. 1917-1920.

* cited by examiner

*Primary Examiner* — Thaian N Ton
*Assistant Examiner* — Titilayo Moloye
(74) *Attorney, Agent, or Firm* — Quarles & Brady LLP

(57) ABSTRACT

Vitronectin-derived cell culture substrates and methods of using the same for culturing pluripotent stem cells are presented.

15 Claims, 9 Drawing Sheets

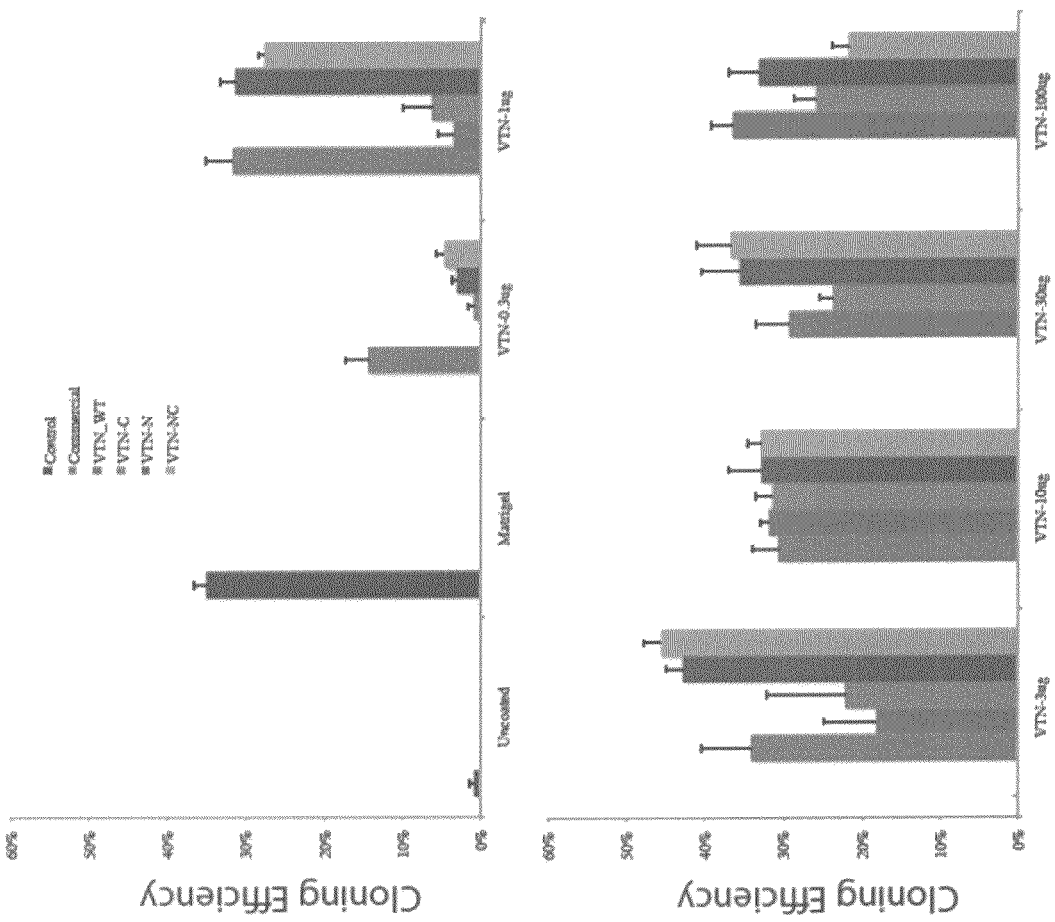

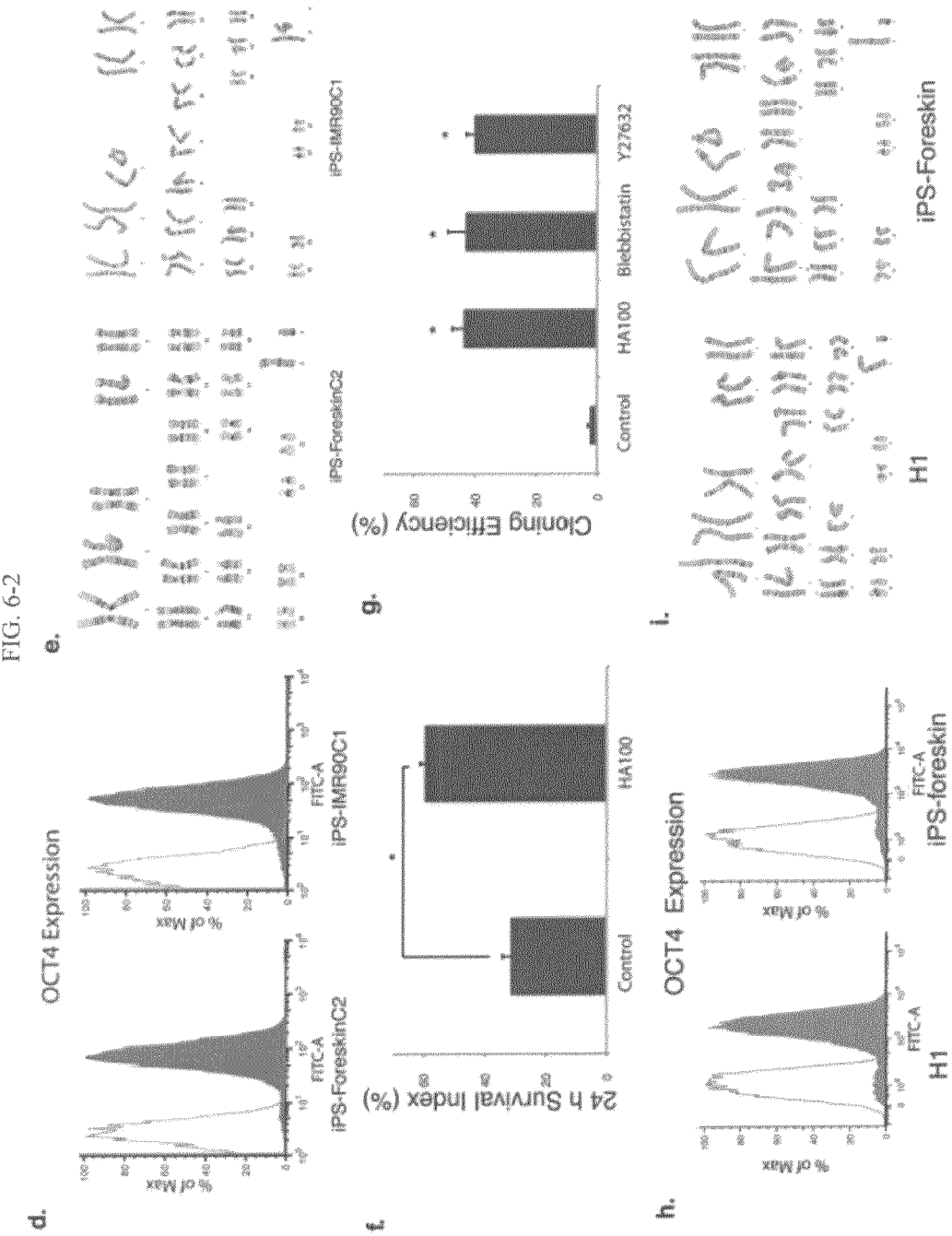

SEQUENCE LISTING

<160> NUMBER OF SEQ ID NOS: 8

<210> SEQ ID NO 1
<211> LENGTH: 459
<212> TYPE: PRT
<213> ORGANISM: Homo sapiens

<400> SEQUENCE: 1

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
        275                 280                 285

Met Gln Arg Asp Ser Trp Glu Asp Ile Phe Glu Leu Leu Phe Trp Gly
290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
            340                 345                 350

Arg His Arg Asn Arg Lys Gly Tyr Arg Ser Gln Arg Gly His Ser Arg
        355                 360                 365
```

```
Gly Arg Asn Gln Asn Ser Arg Arg Pro Ser Arg Ala Thr Trp Leu Ser
    370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Phe Ser Gly Asp Lys Tyr Tyr Arg Val Asn Leu Arg Thr
                420                 425                 430

Arg Arg Val Asp Thr Val Asp Pro Tyr Pro Arg Ser Ile Ala Gln
                435                 440                 445

Tyr Trp Leu Gly Cys Pro Ala Pro Gly His Leu
    450                 455

<210> SEQ ID NO 2
<211> LENGTH: 417
<212> TYPE: PRT
<213> ORGANISM: Artificial Sequence
<220> FEATURE:
<223> OTHER INFORMATION: Synthetic peptide

<400> SEQUENCE: 2

Val Thr Arg Gly Asp Val Phe Thr Met Pro Glu Asp Glu Tyr Thr Val
1               5                   10                  15

Tyr Asp Asp Gly Glu Glu Lys Asn Asn Ala Thr Val His Glu Gln Val
                20                  25                  30

Gly Gly Pro Ser Leu Thr Ser Asp Leu Gln Ala Gln Ser Lys Gly Asn
            35                  40                  45

Pro Glu Gln Thr Pro Val Leu Lys Pro Glu Glu Ala Pro Ala Pro
50                  55                  60

Glu Val Gly Ala Ser Lys Pro Glu Gly Ile Asp Ser Arg Pro Glu Thr
65                  70                  75                  80

Leu His Pro Gly Arg Pro Gln Pro Pro Ala Glu Glu Leu Cys Ser
                85                  90                  95

Gly Lys Pro Phe Asp Ala Phe Thr Asp Leu Lys Asn Gly Ser Leu Phe
                100                 105                 110

Ala Phe Arg Gly Gln Tyr Cys Tyr Glu Leu Asp Glu Lys Ala Val Arg
                115                 120                 125

Pro Gly Tyr Pro Lys Leu Ile Arg Asp Val Trp Gly Ile Glu Gly Pro
                130                 135                 140

Ile Asp Ala Ala Phe Thr Arg Ile Asn Cys Gln Gly Lys Thr Tyr Leu
145                 150                 155                 160

Phe Lys Gly Ser Gln Tyr Trp Arg Phe Glu Asp Gly Val Leu Asp Pro
                165                 170                 175

Asp Tyr Pro Arg Asn Ile Ser Asp Gly Phe Asp Gly Ile Pro Asp Asn
                180                 185                 190

Val Asp Ala Ala Leu Ala Leu Pro Ala His Ser Tyr Ser Gly Arg Glu
                195                 200                 205

Arg Val Tyr Phe Phe Lys Gly Lys Gln Tyr Trp Glu Tyr Gln Phe Gln
                210                 215                 220

His Gln Pro Ser Gln Glu Glu Cys Glu Gly Ser Ser Leu Ser Ala Val
225                 230                 235                 240

Phe Glu His Phe Ala Met Met Gln Arg Asp Ser Trp Glu Asp Ile Phe
                245                 250                 255

Glu Leu Leu Phe Trp Gly Arg Thr Ser Ala Gly Thr Arg Gln Pro Gln
                260                 265                 270
```

```
Phe Ile Ser Arg Asp Trp His Gly Val Pro Gly Gln Val Asp Ala Ala
            275                 280                 285

Met Ala Gly Arg Ile Tyr Ile Ser Gly Met Ala Pro Arg Pro Ser Leu
    290                 295                 300

Ala Lys Lys Gln Arg Phe Arg His Arg Asn Arg Lys Gly Tyr Arg Ser
305                 310                 315                 320

Gln Arg Gly His Ser Arg Gly Arg Asn Gln Asn Ser Arg Arg Pro Ser
                325                 330                 335

Arg Ala Thr Trp Leu Ser Leu Phe Ser Ser Glu Glu Ser Asn Leu Gly
            340                 345                 350

Ala Asn Asn Tyr Asp Asp Tyr Arg Met Asp Trp Leu Val Pro Ala Thr
        355                 360                 365

Cys Glu Pro Ile Gln Ser Val Phe Phe Phe Ser Gly Asp Lys Tyr Tyr
    370                 375                 380

Arg Val Asn Leu Arg Thr Arg Arg Val Asp Thr Val Asp Pro Pro Tyr
385                 390                 395                 400

Pro Arg Ser Ile Ala Gln Tyr Trp Leu Gly Cys Pro Ala Pro Gly His
                405                 410                 415

Leu

<210> SEQ ID NO 3
<211> LENGTH: 379
<212> TYPE: PRT
<213> ORGANISM: Artificial Sequence
<220> FEATURE:
<223> OTHER INFORMATION: Synthetic peptide

<400> SEQUENCE: 3

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
```

```
               210                 215                 220
Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
                260                 265                 270

Glu Cys Glu Gly Ser Ser Leu Ser Ala Val Phe Glu His Phe Ala Met
                275                 280                 285

Met Gln Arg Asp Ser Trp Glu Asp Ile Phe Glu Leu Leu Phe Trp Gly
            290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
                340                 345                 350

Arg His Arg Asn Arg Lys Gly Tyr Arg Ser Gln Arg Gly His Ser Arg
                355                 360                 365

Gly Arg Asn Gln Asn Ser Arg Arg Pro Ser Arg
                370                 375

<210> SEQ ID NO 4
<211> LENGTH: 337
<212> TYPE: PRT
<213> ORGANISM: Artificial Sequence
<220> FEATURE:
<223> OTHER INFORMATION: Synthetic peptide

<400> SEQUENCE: 4

Val Thr Arg Gly Asp Val Phe Thr Met Pro Glu Asp Glu Tyr Thr Val
1               5                   10                  15

Tyr Asp Asp Gly Glu Glu Lys Asn Asn Ala Thr Val His Glu Gln Val
                20                  25                  30

Gly Gly Pro Ser Leu Thr Ser Asp Leu Gln Ala Gln Ser Lys Gly Asn
            35                  40                  45

Pro Glu Gln Thr Pro Val Leu Lys Pro Glu Glu Ala Pro Ala Pro
50                  55                  60

Glu Val Gly Ala Ser Lys Pro Glu Gly Ile Asp Ser Arg Pro Glu Thr
65                  70                  75                  80

Leu His Pro Gly Arg Pro Gln Pro Pro Ala Glu Glu Leu Cys Ser
                85                  90                  95

Gly Lys Pro Phe Asp Ala Phe Thr Asp Leu Lys Asn Gly Ser Leu Phe
                100                 105                 110

Ala Phe Arg Gly Gln Tyr Cys Tyr Glu Leu Asp Glu Lys Ala Val Arg
            115                 120                 125

Pro Gly Tyr Pro Lys Leu Ile Arg Asp Val Trp Gly Ile Glu Gly Pro
            130                 135                 140

Ile Asp Ala Ala Phe Thr Arg Ile Asn Cys Gln Gly Lys Thr Tyr Leu
145                 150                 155                 160

Phe Lys Gly Ser Gln Tyr Trp Arg Phe Glu Asp Gly Val Leu Asp Pro
                165                 170                 175

Asp Tyr Pro Arg Asn Ile Ser Asp Gly Phe Asp Gly Ile Pro Asp Asn
                180                 185                 190

Val Asp Ala Ala Leu Ala Leu Pro Ala His Ser Tyr Ser Gly Arg Glu
```

```
                195                 200                 205
Arg Val Tyr Phe Phe Lys Gly Lys Gln Tyr Trp Glu Tyr Gln Phe Gln
            210                 215                 220

His Gln Pro Ser Gln Glu Glu Cys Glu Gly Ser Ser Leu Ser Ala Val
225                 230                 235                 240

Phe Glu His Phe Ala Met Met Gln Arg Asp Ser Trp Glu Asp Ile Phe
                245                 250                 255

Glu Leu Leu Phe Trp Gly Arg Thr Ser Ala Gly Thr Arg Gln Pro Gln
            260                 265                 270

Phe Ile Ser Arg Asp Trp His Gly Val Pro Gly Gln Val Asp Ala Ala
                275                 280                 285

Met Ala Gly Arg Ile Tyr Ile Ser Gly Met Ala Pro Arg Pro Ser Leu
290                 295                 300

Ala Lys Lys Gln Arg Phe Arg His Arg Asn Arg Lys Gly Tyr Arg Ser
305                 310                 315                 320

Gln Arg Gly His Ser Arg Gly Arg Asn Gln Asn Ser Arg Arg Pro Ser
                325                 330                 335

Arg
```

<210> SEQ ID NO 5
<211> LENGTH: 1380
<212> TYPE: DNA
<213> ORGANISM: Homo sapiens

<400> SEQUENCE: 5

```
gaccaagagt catgcaaggg ccgctgcact gagggcttca acgtggacaa gaagtgccag    60
tgtgacgagc tctgctctta ctaccagagc tgctgcacag actatacggc tgagtgcaag   120
ccccaagtga ctcgcgggga tgtgttcact atgccgagg atgagtacac ggtctatgac    180
gatggcgagg agaaaaacaa tgccactgtc catgaacagg tggggggccc ctccctgacc   240
tctgacctcc aggcccagtc caaagggaat cctgagcaga cacctgttct gaaacctgag   300
gaagaggccc ctgcgcctga ggtgggcgcc tctaagcctg aggggataga ctcaaggcct   360
gagacccttc atccagggag acctcagccc cagcagagg aggagctgtg cagtgggaag   420
cccttcgacg ccttcaccga cctcaagaac ggttccctct ttgccttccg agggcagtac   480
tgctatgaac tggacgaaaa ggcagtgagg cctgggtacc ccaagctcat ccgagatgtc   540
tggggcatcg agggccccat cgatgccgcc ttcacccgca tcaactgtca ggggaagacc   600
tacctcttca agggtagtca gtactggcgc tttgaggatg tgtcctgga ccctgattac    660
ccccgaaata tctctgacgg cttcgatggc atcccggaca acgtggatgc agccttggcc   720
ctccctgccc atagctacag tggccggag cgggtctact tcttcaaggg gaaacagtac    780
tgggagtacc agttccagca ccagcccagt caggaggagt gtgaaggcag ctccctgtcg   840
gctgtgtttg aacactttgc catgatgcag cggacagct gggaggacat cttcgagctt    900
ctcttctggg gcagaacctc tgctggtacc agacagcccc agttcattag ccgggactgg   960
cacggtgtgc cagggcaagt ggacgcagcc atggctggcc gcatctacat ctcaggcatg  1020
gcacccgcc cctccttggc caagaaacaa aggtttaggc atcgcaaccg caaaggctac  1080
cgttcacaac gaggccacag ccgtggccgc aaccagaact cccgccggcc atcccgcgcc  1140
acgtggctgt ccttgttctc cagtgaggag agcaacttgg gagccaacaa ctatgatgac  1200
tacaggatgg actggcttgt gcctgccacc tgtgaaccca tccagagtgt cttcttcttc  1260
tctggagaca gtactaccg agtcaatctt cgcacacggc gagtggacac tgtggaccct  1320
```

```
cctacccac gctccatcgc tcagtactgg ctgggctgcc cagctcctgg ccatctgtag   1380
```

<210> SEQ ID NO 6
<211> LENGTH: 1254
<212> TYPE: DNA
<213> ORGANISM: Artificial Sequence
<220> FEATURE:
<223> OTHER INFORMATION: Synthetic oligonucleotide

<400> SEQUENCE: 6

```
gtgactcgcg gggatgtgtt cactatgccg gaggatgagt acacggtcta tgacgatggc    60
gaggagaaaa acaatgccac tgtccatgaa caggtggggg cccctccct gacctctgac   120
ctccaggccc agtccaaagg gaatcctgag cagacacctg ttctgaaacc tgaggaagag   180
gccctgcgc ctgaggtggg cgcctctaag cctgagggga tagactcaag gcctgagacc   240
cttcatccag ggagacctca gcccccagca gaggaggagc tgtgcagtgg gaagcccttc   300
gacgccttca ccgacctcaa gaacggttcc ctctttgcct tccgagggca gtactgctat   360
gaactggacg aaaaggcagt gaggcctggg taccccaagc tcatccgaga tgtctggggc   420
atcgagggcc ccatcgatgc cgccttcacc gcatcaact gtcaggggaa gacctacctc   480
ttcaagggta gtcagtactg gcgctttgag gatggtgtcc tggaccctga ttaccccga   540
aatatctctg acggcttcga tggcatcccg gacaacgtgg atgcagcctt ggccctccct   600
gcccatagct acagtggccg ggagcgggtc tacttcttca aggggaaaca gtactgggag   660
taccagttcc agcaccagcc cagtcaggag gagtgtgaag cagctccct gtcggctgtg   720
tttgaacact ttgccatgat gcagcgggac agctgggagg acatcttcga gcttctcttc   780
tggggcagaa cctctgctgg taccagacag ccccagttca ttagccggga ctggcacggt   840
gtgccagggc aagtggacgc agccatggct ggccgcatct acatctcagg catggcaccc   900
cgcccctcct tggccaagaa acaaaggttt aggcatcgca accgcaaagg ctaccgttca   960
caacgaggcc acagccgtgg ccgcaaccag aactcccgcc ggccatcccg cgccacgtgg  1020
ctgtccttgt tctccagtga ggagagcaac ttgggagcca caactatga tgactacagg  1080
atggactggc ttgtgcctgc cacctgtgaa cccatccaga gtgtcttctt cttctctgga  1140
gacaagtact accgagtcaa tcttcgcaca cggcgagtgg acactgtgga ccctccctac  1200
ccacgctcca tcgctcagta ctggctgggc tgcccagctc tggccatct gtag         1254
```

<210> SEQ ID NO 7
<211> LENGTH: 1137
<212> TYPE: DNA
<213> ORGANISM: Artificial Sequence
<220> FEATURE:
<223> OTHER INFORMATION: Synthetic oligonucleotide

<400> SEQUENCE: 7

```
gaccaagagt catgcaaggg ccgctgcact gagggcttca acgtggacaa gaagtgccag    60
tgtgacgagc tctgctctta ctaccagagc tgctgcacag actatacggc tgagtgcaag   120
ccccaagtga ctcgcgggga tgtgttcact atgccggagg atgagtacac ggtctatgac   180
gatggcgagg agaaaaacaa tgccactgtc catgaacagg tggggggccc ctccctgacc   240
tctgacctcc aggcccagtc caagggaat cctgagcaga cacctgttct gaaacctgag   300
gaagaggccc ctgcgcctga ggtgggcgcc tctaagcctg aggggataga ctcaaggcct   360
gagacccttc atccagggag acctcagccc ccagcagagg aggagctgtg cagtgggaag   420
```

-continued

```
ccccttcgacg ccttcaccga cctcaagaac ggttccctct ttgccttccg agggcagtac    480
tgctatgaac tggacgaaaa ggcagtgagg cctgggtacc ccaagctcat ccgagatgtc    540
tggggcatcg agggccccat cgatgccgcc ttcacccgca tcaactgtca ggggaagacc    600
tacctcttca agggtagtca gtactggcgc tttgaggatg gtgtcctgga ccctgattac    660
ccccgaaata tctctgacgg cttcgatggc atcccggaca acgtggatgc agccttggcc    720
ctccctgccc atagctacag tggccgggag cgggtctact tcttcaaggg gaaacagtac    780
tgggagtacc agttccagca ccagcccagt caggaggagt gtgaaggcag ctccctgtcg    840
gctgtgtttg aacactttgc catgatgcag cgggacagct gggaggacat cttcgagctt    900
ctcttctggg gcagaacctc tgctggtacc agacagcccc agttcattag ccgggactgg    960
cacggtgtgc cagggcaagt ggacgcagcc atggctggcc gcatctacat ctcaggcatg   1020
gcaccccgcc cctccttggc caagaaacaa aggtttaggc atcgcaaccg caaaggctac   1080
cgttcacaac gaggccacag ccgtggccgc aaccagaact cccgccggcc atcccgc      1137
```

<210> SEQ ID NO 8
<211> LENGTH: 1011
<212> TYPE: DNA
<213> ORGANISM: Artificial Sequence
<220> FEATURE:
<223> OTHER INFORMATION: Synthetic oligonucleotide

<400> SEQUENCE: 8

```
gtgactcgcg gggatgtgtt cactatgccg gaggatgagt acacggtcta tgacgatggc     60
gaggagaaaa acaatgccac tgtccatgaa caggtggggg gcccctccct gacctctgac    120
ctccaggccc agtccaaagg gaatcctgag cagacacctg ttctgaaacc tgaggaagag    180 gccсctcgcgc ctgaggtggg cgcctctaag cctgagggga tagactcaag gcctgagacc    240
cttcatccag ggagacctca gcccccagca gaggaggagc tgtgcagtgg gaagcccttc    300
gacgccttca ccgacctcaa gaacggttcc ctctttgcct tccgagggca gtactgctat    360
gaactggacg aaaaggcagt gaggcctggg taccccaagc tcatccgaga tgtctggggc    420
atcgagggcc ccatcgatgc cgccttcacc cgcatcaact gtcaggggaa gacctacctc    480 ttcaaggggta gtcagtactg gcgctttgag gatggtgtcc tggaccctga ttacccccga    540
aatatctctg acggcttcga tggcatcccg gacaacgtgg atgcagcctt ggccctccct    600
gcccatagct acagtggccg ggagcgggtc tacttcttca aggggaaaca gtactgggag    660
taccagttcc agcaccagcc cagtcaggag gagtgtgaag gcagctccct gtcggctgtg    720
tttgaacact ttgccatgat gcagcgggac agctgggagg acatcttcga gcttctcttc    780
tggggcagaa cctctgctgg taccagacag ccccagttca ttagccggga ctggcacggt    840
gtgccagggc aagtggacgc agccatggct ggccgcatct acatctcagg catggcaccc    900
cgcccctcct tggccaagaa acaaaggttt aggcatcgca accgcaaagg ctaccgttca    960
caacgaggcc acagccgtgg ccgcaaccag aactcccgcc ggccatcccg c           1011
```

VITRONECTIN-DERIVED CELL CULTURE SUBSTRATE AND USES THEREOF

CROSS-REFERENCE TO RELATED APPLICATION

This application claims priority to U.S. Provisional Application Ser. No. 61/483,521, filed May 6, 2011, which is incorporated herein by reference in its entirety.

STATEMENT REGARDING FEDERALLY SPONSORED RESEARCH OR DEVELOPMENT

This invention was made with government support under GM081629 and ES017166 awarded by the National Institutes of Health. The government has certain rights in the invention.

BACKGROUND

The invention relates generally to vitronectin-derived cell culture substrates and methods of using the same for culturing pluripotent stem cells.

Pluripotent stem cells, such as embryonic stem (ES) cells and induced pluripotent stem (iPS) cells, are characterized by self-renewal without differentiation and the ability to differentiate into cells of all three germ layers (Evans & Kaufman, Nature 292:154-156 (1981)). An important aspect of culturing pluripotent stem cells are the culture conditions themselves. Successful maintenance and experimental use of pluripotent stem cells includes culture conditions that provide growth factors and appropriate substrates to sustain viability and pluripotency.

Pluripotent stem cell culture methods have evolved considerably in an effort to define conditions and reduce inter-culture variability. Completely-defined growth media, such as TESR™ (Ludwig et al., Nat. Methods 3:637-646 (2006)), were developed to provide controllable and reproducible sources of basic nutrients and growth factors for survival and expansion of pluripotent cells to directly determine how pluripotent stem cells grow and differentiate. However, experimental variability is introduced by the use of varying and undefined substrates. According to conventional culture methods, pluripotent stem cells are grown on a layer of feeder cells or on complex artificial matrices, such as MATRIGEL™. Both feeder layers and complex matrices fluctuate unpredictably in their composition. Because the precise composition of these matrices cannot be determined, it is difficult to predict how the substrate interacts with the cell or media components.

To reduce this compositional variability, pluripotent cells have recently been cultured on isolated or recombinant extracellular matrix proteins (Miyazaki et al., Biochem. Biophys. Res. Commun. 375:27-32 (2008); Braam et al., Stem Cells 26:2257-2265 (2008)). Examples of extracellular matrix proteins successfully used as substrates for pluripotent cell culture include laminin, fibronectin, E-cadherin, and vitronectin.

Vitronectin has been successfully employed as an in vitro substrate for many cell types, including human pluripotent stem cells. Immature vitronectin is converted to its mature form when a 19-amino acid signal peptide at its N-terminus is cut off during the process of protein maturation to form mature vitronectin. Mature vitronectin, herein referred to as vitronectin, is a 459 amino acid glycoprotein of approximately 75 kDa that contains an amino-terminal domain (N-terminal amino acids 1-44), which includes a somatomedin B domain, followed by a Arg-Gly-Asp (RGD) sequence, a central domain rich in hydrophobic amino acids (central amino acids 131-342), and a carboxyl-terminal domain (C-terminal amino acids 379-459). The N-terminal somatomedin B domain (SMB) and the C-terminal V10 domain are functional domains in vitronectin.

The high cost and low yield associated with producing vitronectin in animal cell cultures limit use of the protein in animal cell culture methods. Also, vitronectin production from animal cell culture bears the inherent risk of animal protein contamination. While vitronectin can be produced by recombinant methods, recombinant vitronectin has shown very low activity in cell culture.

Pluripotent stem cells are most useful for research and clinical application when the conditions used to derive and culture them are fully defined and controlled. Accordingly, there is a need in the art for substrates free of components that introduce inconsistencies to maintain control over pluripotent cell culture conditions. Specifically, there is a need in the art for pluripotent cell culture substrates containing only those components that support pluripotent cell function. Further, the art seeks fully-defined substrates that can be produced easily, cheaply, and in large quantities without contamination of animal protein.

BRIEF SUMMARY OF THE INVENTION

The invention relates generally to substrates, compositions, and methods for deriving and culturing pluripotent cells, and more particularly, to fully-defined substrates comprising vitronectin polypeptide variants for deriving and culturing pluripotent cells.

In a first aspect, the present invention is summarized as a method for culturing pluripotent stem cells on a substrate comprising a vitronectin polypeptide variant. The vitronectin polypeptide variant is characterized by a terminal truncation at its N-terminus, at its C-terminus, or at both its N- and C-termini, relative to a full-length vitronectin polypeptide.

In some embodiments of the first aspect, a vitronectin polypeptide variant has the amino acid sequence set forth as SEQ ID NO:2, SEQ ID NO:3, or SEQ ID NO:4.

In some embodiments of the first aspect, the pluripotent stem cells are cultured under fully-defined medium conditions.

In some embodiments of the first aspect, the substrate is substantially free of xenogenic contamination with regard to the pluripotent stem cells.

In a second aspect, the present invention is summarized as a method for deriving an induced pluripotent stem (iPS) cell by culturing and reprogramming a somatic cell on a substrate comprising a vitronectin polypeptide variant having a terminal truncation relative to a full-length vitronectin polypeptide such as to derive an iPS cell.

In a third aspect, the present invention is summarized as a method for cloning a pluripotent cell by plating a pluripotent cell at cloning density on a substrate comprising a vitronectin polypeptide variant characterized by a terminal truncation of either its amino-terminus, its carboxyl-terminus, or both its amino- and carboxy-termini relative to a full-length vitronectin polypeptide.

In a fourth aspect, the present invention is summarized as a substrate suitable for pluripotent stem cell culture, the substrate comprising a vitronectin polypeptide variant having a terminal truncation relative to a full-length vitronectin polypeptide.

In some embodiments of the fourth aspect, the substrate is characterized as having an enhanced ability, as compared to full-length vitronectin, to support pluripotent cell viability, proliferation, pluripotency, and cloning.

In a fifth aspect, the present invention is summarized as an isolated nucleic acid molecule comprising a nucleic acid sequence that encodes a vitronectin polypeptide variant having a terminal truncation relative to a full-length vitronectin polypeptide.

In some embodiments of the fifth aspect, the isolated nucleic acid comprises the nucleic acid sequence set forth as SEQ ID NO:6, SEQ ID NO:7, or SEQ ID NO:8.

In a sixth aspect, the present invention is summarized as a vector comprising a nucleic acid sequence that encodes a vitronectin polypeptide variant having a terminal truncation relative to a full-length vitronectin polypeptide, the nucleic acid sequence being operably linked to an expression control sequence.

In a seventh aspect, the present invention is summarized as a bacterial cell comprising a vector not natively present in the bacterial cell where the vector comprises a nucleic acid sequence that encodes a vitronectin polypeptide variant having a terminal truncation relative to a full-length vitronectin polypeptide, the nucleic acid sequence being operably linked to an expression control sequence.

The methods and compositions described herein are useful in a variety of applications that include culturing pluripotent stem cells, such as pluripotent cell maintenance, differentiation, and induced pluripotent cell derivation.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to preclude the invention from covering all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1:
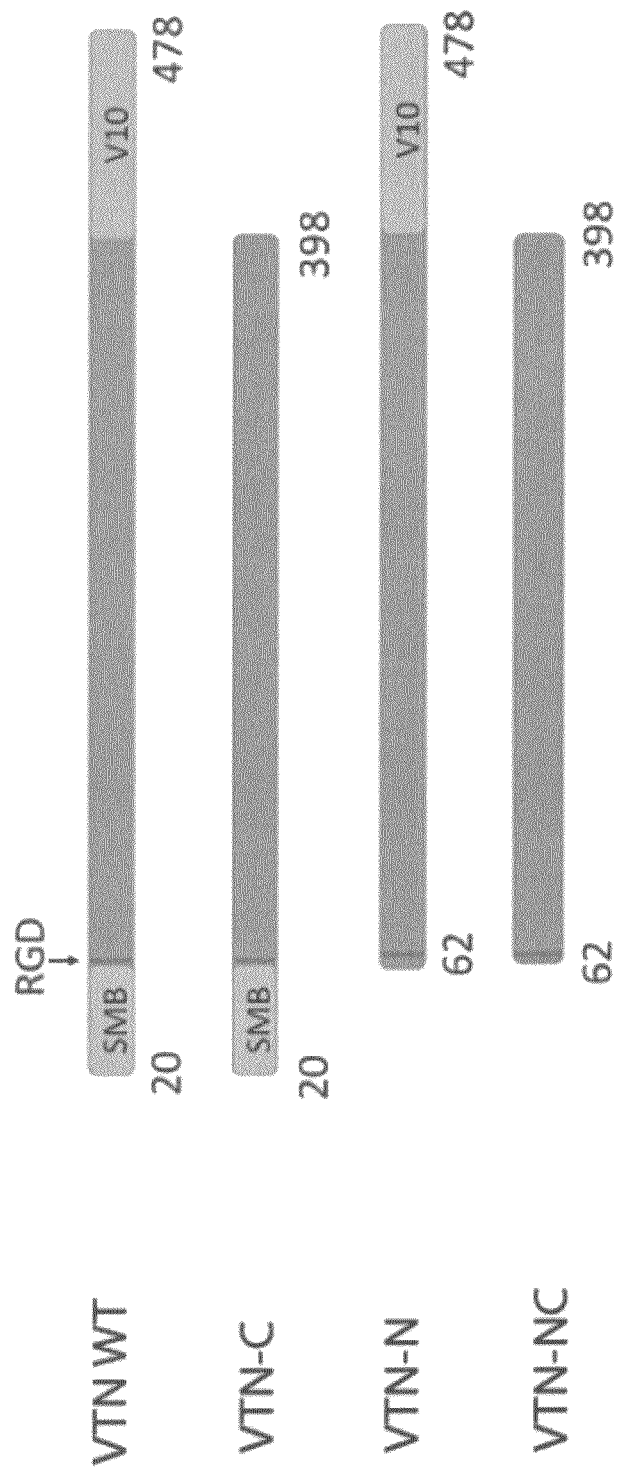
FIG. 1 shows schematic diagrams of vitronectin (VTN WT) and vitronectin variants having a truncated C-terminus (VTN-C), a truncated N-terminus (VTN-N), or a truncated N- and C-terminus and N-and C-terminal deletion mutant (VTN-NC). Numbers indicate amino acid positions; SMB=somatomedin B domain; V10=V10 subunit.
Figure 2:
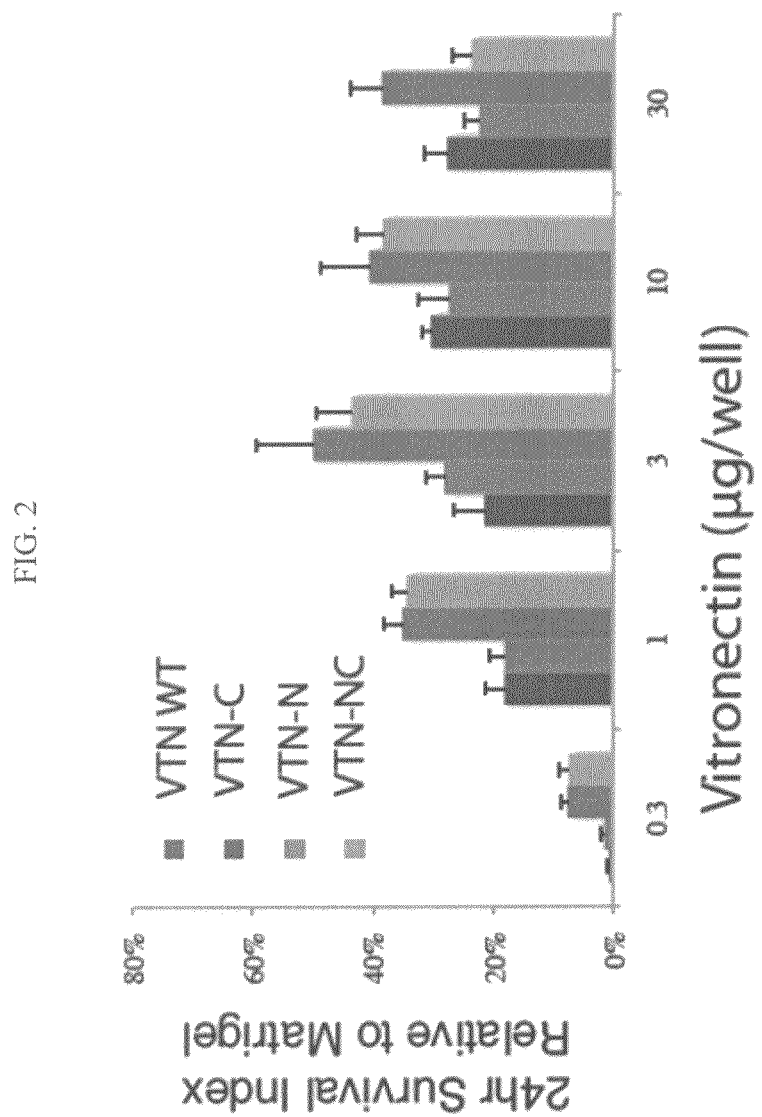
FIG. 2 illustrates the survival index of cells cultured on various matrices, relative to cells cultured on MATRIGEL™, after 24 hours. Abbreviations are as set forth in FIG. 1.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE INVENTION

The present invention relates to the inventors' observation that polypeptide variants of the large glycoprotein, vitronectin, support pluripotent stem cell cultures at least as efficiently as conventionally used matrices, such as MATRIGEL™. Mature vitronectin is a 459 amino acid glycoprotein of approximately 75 kDa that contains multiple structural and functional domains that promote interactions with itself and other ligands in the extracellular matrix and in the circulatory system. For example, mature vitronectin contains an amino-terminal domain (comprising about 42-44 consecutive amino acids), which includes a somatomedin B domain (SMB). Adjacent to the N-terminal domain is an Arg-Gly-Asp (RGD) sequence which provides a binding site for host cell integrin receptors. Mature vitronectin also contains a central domain rich in hydrophobic amino acids (comprising about 211 consecutive amino acids at approximately positions 131-342) and a carboxyl-terminal domain (comprising about 79-80 consecutive amino acids). The N-terminal SMB domain and the C-terminal V10 domain are functional domains in vitronectin. For example, the 44-amino acid SMB domain, which includes a framework of four disulfide bonds formed by a knot of 8 cysteine residues, contains binding sites important for the glycoprotein's adhesive properties. Recent reports demonstrate that the N-terminal vitronectin SMB domain, together with the vitronectin RGD peptide, supports human embryonic stem (hES) cell growth and pluripotency, suggesting special importance of the vitronectin N-terminal domain for hES cell adhesion and growth (Prowse et al., *Biomaterials* 31:8281-8288 (2010)).

As used herein, the term "pluripotent stem cell" refers to a cell capable of differentiating into cells of all three germ layers. Examples of pluripotent cells include embryonic stem (ES) cells and induced pluripotent stem (iPS) cells. As used herein, "iPS cells" refer to pluripotent cells derived from somatic cells that display characteristics similar to higher potency cells, such as ES cells, as described herein. The cells can be obtained by reprogramming non-pluripotent (e.g., multipotent or somatic) cells (U.S. Patent App. No. 2010/0184227 and U.S. Patent App. No. U.S. 2008/0233610, each of which is incorporated herein by reference as if set forth in its entirety). The pluripotent cells used in the disclosed methods can be obtained from a human or non-human animal, preferably, from a human or non-human primate.

As described above, growing pluripotent cells, like ES cells, in culture depends upon culture conditions that support both viability and pluripotency. As used herein, "viability" means the state of being viable. Pluripotent stem cells that are viable attach to the cell plate surface and do not stain with the dye propidium iodide absent membrane disruption. Short term viability relates to the first 24 hours after plating the cells in culture. Typically, the cells do not proliferate in that time.

Unpredictable and uncontrollable variations in culture conditions, such as those introduced by complex substrates, contribute to undesirable variations between cultures. One of skill in the art recognizes the advantageous efficiency of reducing inter-culture variations that are the result of culture conditions. While fully-defined media are available, a need still remains for fully defined substrates that support pluripotent stem cells and which can be produced inexpensively and free of animal protein contaminants. As used herein, the term "substrate" refers to a material or composition adapted for use in the propagation and cultivation of stem cells (e.g., embryonic stem cells, iPS cells). Commonly, substrates provide a material or composition for adhesion of cells in culture.

The invention relates to new cell culture substrates comprising at least one vitronectin polypeptide variant having a terminal truncation relative to a full-length vitronectin polypeptide. As used herein, "vitronectin polypeptide variant" refers to a vitronectin protein that lacks at least 5-100 amino acids from its amino-terminus or from its carboxyl-terminus or from both termini relative to a full-length vitronectin polypeptide. In some cases, a vitronectin polypeptide variant is identified by the number of amino acids truncated relative to a full-length vitronectin polypeptide having the amino acid sequence set forth as SEQ ID NO:1. For example, in an exemplary embodiment, a vitronectin polypeptide variant will have a truncation that deletes some or all of amino acids 1-44, where the amino acids are numbered relative to the amino acid sequence of full-length vitronectin set forth as SEQ ID NO:1, and where the truncation begins at the N-terminus and removes as many as 44 consecutive amino acids (e.g., the 42-44 amino acids defining the N-terminus of vitronectin). In another exemplary embodiment, a vitronectin polypeptide will have a truncation that deletes some or all of amino acids 379-459, numbered relative to the amino acid sequence of full-length vitronectin set forth as SEQ ID NO:1, where the truncation begins at amino acid position 379 and removes as many as 80 consecutive amino acids up to and including the amino acid at position 459 (e.g., the 80 amino acids defining the C-terminus of vitronectin).

The amino terminus can be defined to include the about 42-44 consecutive amino acids N-terminal to the RGD peptide sequence. In human vitronectin, the first 42-44 consecutive amino acids adjacent to the N-terminus define the N-terminal domain. As used herein, "terminal truncation" refers to an omission, deletion, or removal of at least amino acids from either the C-terminal or the N-terminal end, or from both ends, of the protein relative to a full-length vitronectin polypeptide having the amino acid sequence set forth as SEQ ID NO:1. Specifically contemplated are also vitronectin polypeptide variants having N-terminal and C-terminal deletions relative to full-length vitronectin, e.g., a deletion of some or all of amino acids 1-44 and a deletion of some or all of amino acids 379-459, where the amino acids are numbered relative to the amino acid sequence of full-length vitronectin set forth as SEQ ID NO:1. As used herein, the term "about" refers to a value or values within 5% of a stated range or within 5% of a stated time frame.

In some embodiments, a vitronectin polypeptide variant has an amino acid sequence as set forth as SEQ ID NO:2, SEQ ID NO:3, or SEQ ID NO:4. A skilled artisan understands that polypeptide sequences presented herein can vary somewhat, whether as a result, e.g., of sequencing error or allelic variation or duplication, from the sequence presented while still retaining their essential nature. Because of the degeneracy in the genetic code, the polypeptide sequences disclosed can also be encoded by a variety of polynucleotide sequences, all of which are within the scope of the invention. Polypeptides of the invention include polymorphic variants, alleles, mutants, and interspecies homologs.

Vitronectin polypeptide variants having N- or C-terminal truncations can be isolated from a natural source or be synthesized. One of skill in the art recognizes the advantageous efficiency of producing recombinant proteins, rather than isolating proteins from an animal source, to improve efficiency and to minimize possible animal protein contamination.

According to some embodiments, the protein can be truncated by genetically engineering a sequence encoding a vitronectin polypeptide variant such that it no longer encodes a portion of the N- and/or C-terminus The sequence can also be altered such that a portion of the N- and/or C-terminus is removed during RNA splicing. The protein can also be truncated by post translational modification, such as by chemical treatment or by enzymatic cleavage.

In a preferred embodiment, the vitronectin polypeptide variants are produced by introducing a vector encoding at least one vitronectin polypeptide variant into a host cell capable of expressing the encoded variant on the vector to produce the protein. The vector includes a sequence encoding at least one vitronectin polypeptide variant, where the sequence is operably linked to an expression control element or expression control sequence for expression in the host cell. Expression control elements or sequences appropriate for the methods provided herein can include, without limitation, promoters (e.g., transcriptional promoters), enhancers, and upstream or downstream untranslated sequences. Suitable host cells include bacterial cells, such as *E. coli*, and eukaryotic cells, such as yeast cells, insect cells, avian cells, or mammalian cells. The vitronectin polypeptide variant can then be isolated from the host cells by any method suitable for recovering functional protein.

Growth on the disclosed vitronectin substrates advantageously minimizes inter-culture variations attributable to variable substrate compositions associated with complex undefined matrices. In a preferred embodiment, the substrates are substantially free of factors not required to achieve a particular culture objective. Examples of culture objectives include, but are not limited to, cell survival, passaging, proliferation, pluripotency during short-term and extended growth, cloning, and iPS cell derivation.

As used herein, "short term growth" means cell proliferation for 4-5 days in culture. As used herein, "extended growth" means growth for at least five passages, preferably more than twenty passages (e.g., about 2-3 months). As used herein, "cloning" means a process of initiating a cell culture from a starting culture, ideally, from a single pluripotent cell or at least from very few cells. As used herein, "iPS cell derivation" means reprogramming a somatic cell to become pluripotent.

In a preferred embodiment, the vitronectin polypeptide variant has an enhanced ability, relative to full-length vitronectin, to support pluripotent stem cells. For example, VTN-N and VTN-NC has a 10-fold increased activity. As used herein, "activity" refers to the ability of vitronectin to support pluripotent cell function, e.g., during culture, growth, cloning, or iPS cell derivation, at a given concentration. Thus, a vitronectin polypeptide variant has an enhanced ability, relative to full-length vitronectin if, e.g., the variant supports greater pluripotent cell growth than vitronectin at the same concentration.

Suitable pluripotent stem cells for use in the methods described herein include embryonic stem cells and induced pluripotent stem cells. As used herein, "iPS cells" refer to cells that are substantially genetically identical to their respective differentiated somatic cell of origin and display characteristics similar to higher potency cells, such as ES cells, as described herein. The cells can be obtained from various differentiated (i.e., non-pluripotent and multipotent) somatic cells.

iPS cells exhibit morphological (i.e., round shape, large nucleoli and scant cytoplasm) and growth properties (i.e., doubling time; ES cells have a doubling time of about seventeen to eighteen hours) akin to ES cells. In addition, iPS cells express pluripotent cell-specific markers (e.g., Oct-4, SSEA-3, SSEA-4, Tra-1-60, Tra-1-81, but not SSEA-1). iPS cells, however, are not immediately derived from embryos and can transiently or stably express one or more copies of selected potency-determining factors at least until they become pluripotent. As used herein, "not immediately derived from embryos" means that the starting cell type for producing iPS cells is a non-pluripotent cell, such as a multipotent cell or terminally differentiated cell, such as somatic cells obtained from a post-natal individual.

In a preferred embodiment, the pluripotent cells are cultured on the vitronectin substrates disclosed herein under defined conditions. Defined conditions can include culturing cells in a defined culture medium. As referred to herein, the term "defined culture medium" refers to a culture medium in which each constituent of the medium is fully disclosed and characterized. Defined culture media that promote long-term culture of undifferentiated pluripotent stem cells are known in the art (e.g., Ludwig et al., *Nat. Methods* 3:637-646 (2006), incorporated herein by reference as if set forth in its entirety). In certain embodiments, a defined cell culture medium consists essentially of no more than the constituents required to achieve a particular cell culture objective. In some cases, a defined culture medium can comprise DMEM/F12 plus a finite number of defined constituents that support human embryonic stem cells and iPS cells. As used herein, the phrase "a medium consisting essentially of" refers to a medium that contains the specified ingredients and those that do not materially affect its basic characteristics. Such defined constituents can be insulin, selenium, transferrin, L-ascorbic acid, FGF2, and TGFβ (or NODAL). Accordingly, a defined culture medium provided herein can be a medium comprising or, in some cases, consisting essentially of insulin, selenium, transferrin, L-ascorbic acid, FGF2, and TGFβ (or NODAL) in DMEM/F12 with pH adjusted with NaHCO$_3$. In preferred embodiments, a defined culture medium can be used to improve the efficiency of human iPS cell derivation from tissue samples such as, for example, dermal biopsy samples. In some cases, a defined culture medium such as E8-based medium can be used for all stages of iPS cell derivation and culture. As described in Example 5, a defined culture medium such as E8-based medium can be suitable for supporting undifferentiated proliferation of ES and iPS cells and/or maintaining pluripotency markers or normal karyotypes over multiple passages (e.g., at least 5, at least 10, at least 15, at least 20, or at least 25 passages). In another preferred embodiment, the culture conditions are substantially free of xenogenic contamination (or "xeno-free") with regard to the pluripotent stem cells. As used herein, the terms "substantially free of xenogenic contamination" and "xeno-free" refer to cell culture conditions substantially free of any cell or cell product of species other than that of the cultured cell.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

The invention will be more fully understood upon consideration of the following non-limiting Examples.

EXAMPLES

Example 1

Vitronectin Expression and Purification

Coding sequences of human vitronectin and three vitronectin variants (having the amino acid endpoints shown in FIG. 1) lacking the N-terminal domain (VTN-N), lacking the C-terminal domain (VTN-C), or lacking the N- and C-terminal domain (VTN-NC) were amplified from cDNA clone purchased from OriGene Technologies, Inc. (Rockville, Md.) and cloned into the NdeI and BamHI sites of a bacterial expression vector (pET3c, Novagen, Inc.). All constructs were verified by sequencing. Proteins were expressed in Rosetta2 (DE3) pLysS E. coli cells (Novagen) cultured in Magic Media (Invitrogen) at 37° C. for 24 hours. The vitronectin proteins were purified essentially as described by Wojciechowski et al., *Protein Expr. Purif.* 36:131-138 (2004), incorporated herein as if set forth in its entirety. Briefly, the E. coli pellet was resuspended in PBS and lysed with FAST-BREAK™ cell lysis reagent (Promega). Insoluble material was pelleted by centrifugation at 10,000 g. The pellet was washed once with PBS-0.5M NaCl and then solubilized in urea buffer (8 M urea, 20 mM Tris pH 7.6, 150 mM NaCl and 3 mM DTT). The solubilized vitronectin was loaded onto a heparin sepharose column and the column was then washed extensively with urea buffer. Protein was eluted with urea buffer +500 mM NaCl and dialyzed into PBS overnight.

Example 2

Pluripotent Cell Survival Assay

Vitronectin variants lacking the N-terminal domain (VTN-N), lacking the C-terminal domain (VTN-C), or lacking the N- and C-terminal domain (VTN-NC) were expressed in E. coli and purified essentially as described in Example 1 and used to coat 12-well plate wells at various concentrations (0.3-30 μg/well). Five-hundred microliters (μL) of medium was loaded into each well of the 12-well plates prior to the addition of cells. Adherent pluripotent cells were dissociated with TrypLE (Invitrogen) for 5 minutes or until fully detached from the culture plates. TrypLE was neutralized by adding an equal volume of media to the culture. The cells were counted, washed, and resuspended in fresh medium at a concentration of 300,000 to 1,000,000 cells/ml. The cells were added onto cell culture plates coated with the various vitronectin proteins and were incubated at 37° C. with 5% O$_2$ and 10% CO$_2$. Cells were again dissociated at various time points using 0.4 ml TrypLE, which was subsequently neutralized with equal volumes of 10% FBS in DMEM. The cells were counted by flow cytometry. 5000 CountBright™ Absolute Counting Beads (Invitrogen) were added to each sample as internal control (approximately 200 beads were counted for each sample). All experiments were performed in triplicate.

Example 3

Enhanced Pluripotent Stem Cell Survival

Vitronectin polypeptide variants lacking the N-terminal domain (VTN-N), lacking the C-terminal domain (VTN-C), or lacking the N- and C-terminal domains (VTN-NC) relative to full-length vitronectin were expressed in E. coli and purified essentially as described in Example 1. Cell survival assays were conducted essentially as described in Example 2. The three vitronectin polypeptide variants were coated onto cell culture plates at concentrations ranging from 1-30 μg/well. Approximately 100,000 H1 cells were plated onto cell culture plates coated with wild-type full-length vitronectin, VTN-N, VTN-C, or VTN-NC in a fully-defined culture medium (DMEM/F12, L-Ascorbic Acid, Selenium, Transferrin, NaHCO3, Insulin, FGF2, and either TGF-β or Nodal) and counted after 24 hours. Survival of cells grown on vitronectin polypeptide variants lacking the N-terminal domain (VTN-N, dark gray) or lacking both N- and C-termini (VTN-NC, light) was significantly enhanced compared to that of cells grown on wild type (VTN-WT, dark) or on the vitronectin polypeptide variant lacking the C-terminus (VTN-C, light gray) (*$p<0.05$, n=3). The vitronectin polypeptide variants also supported cultures of rhesus monkey (Macaca mulatta) ES cells, rhesus iPS cells, and mouse epiblast stem cells (EpiSC) cells.

Example 4

Enhanced Cloning Efficiency

To determine how the various vitronectin variants affect cloning efficiency, the vitronectin polypeptide variants were tested in a cloning assay, essentially as described by Chen et al, *Cell Stem Cell* 7:240-248 (2010), incorporated herein by reference as if set forth in its entirety. Briefly, triplicates for each substrate were prepared in a 12-well plate. Prior to the addition of cells, 500 μL medium was added to each well. Cells were detached from their culture plate and dissociated with TrypLE for 5 minutes or until fully detached. TrypLE was neutralized with equal volumes of basic media, and the cells were counted, washed and then diluted to 5000 cells/mL. 100 μL of this cell suspension (500 cells) was added to each well. Plates were then incubated at 37° C., 5% $O_2$ and 10% $CO_2$ and the medium was changed every 1-2 day(s). After 5-6 days, colonies were stained with an APS kit (Vector Lab) following the manufacturer's instruction and counted.

The cloning efficiencies of cells grown on MATRIGEL™ and cells grown on vitronectin-coated surfaces (FIG. 3) were not significantly different. Notably, significantly lower concentrations of VTN-NC and VTN-N protein, as compared to wild type vitronectin, were sufficient for effective cloning of H1 cells.

Example 5

Albumin-free E8 Medium Supports ES and iPS Cell Culture

Figures 1, 4:
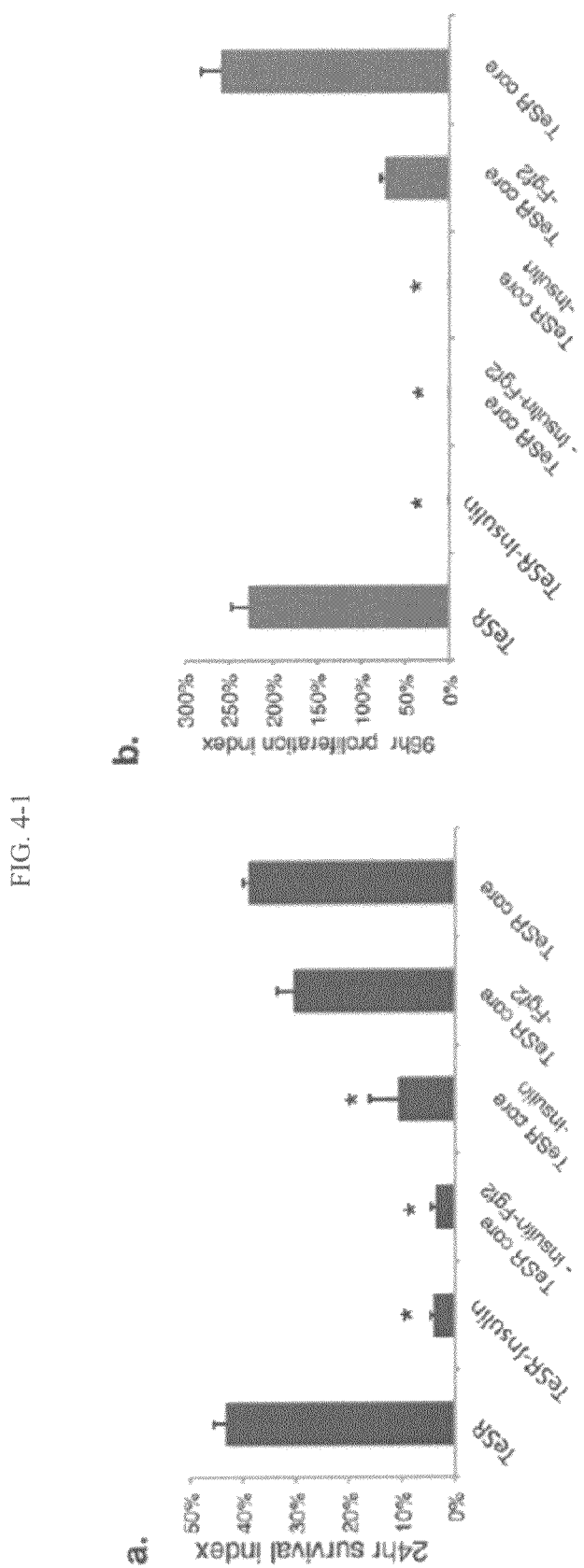
FIG. 4 presents media components supporting human ES cell survival and proliferation. (A) Dissociated H1 ES cells were plated into different media (Table 1) on MATRIGEL-coated plates, and cell survival was measured 24 hours after plating. (*) signifies that the survival index in media with insulin differed significantly (*$p<0.05$, n=3) from the survival in media without insulin. (B) The same ES cells from FIG. 5A were cultured in the same media with daily media change, and proliferation was measured 96 hours after plating. (*) signifies that the survival proliferation index in media with both insulin and FGF2 differs significantly from media without either or both growth factors. (C) Dissociated cells were plated in three different media, and initial survival was measured 22 hours after plating (blue column) Proliferation was measured 129 hours after plating (red column) The three media were TESR™, TESR without L-ascorbic acid (TESR-LAA) and a simplified medium containing DMEM/F 12, $NaHCO_3$ LAA, insulin and FGF2 (*$p<0.05$, n=3). (D) H1 cells were maintained in defined media (DMEM/F12, $NaHCO_3$, Insulin, FGF2 and LAA) for multiple passages with or without selenium. 150,000 starting cells were seeded in each passage on day 0, 4 and 7. (E) Human H1 cells were grown in DMEM/F12, $NaHCO_3$, Insulin, FGF2, LAA and selenium with or without NODAL for four passages, and OCT4 expression was analyzed by FACS. Green peak: anti-OCT4 primary antibody with Alexa-488 secondary antibody; unshaded peak: mouse IgG control. (F) Transferrin was tested with cloning assay in defined media (DMEM/F12, $NaHCO_3$, Insulin, FGF2, LAA, and Selenium); human foreskin iPS cells (Yu et al., Science 318:1917-1920 (2007)) were used in this particular experiment with ROCK inhibitor HA100 (10 μM) in hypoxic conditions (*$p<0.05$, n=3). Similar results were obtained from human ES and other iPS cell lines. (G) E8 medium (Table 1), TESR™ and conditioned medium (CM) were tested by cloning assay with HA100 (*$p<0.05$, n=3). Hypoxia conditions (5% $O_2$ and 10% $CO_2$, red column) and normoxic conditions (5% $CO_2$, blue column) were used in the test (*$p<0.05$, n=3). Similar results were obtained from iPS cell lines. (H) E8 medium and TESR™ were used to culture ES and iPS cells for long-term expansion, and the proliferation dynamics was recorded in the first seven passages. 200,000 H1 and human foreskin iPS cells (Yu et al., Science 324:797-801 (2009)) were plated in each passage in E8 and TESR™ media in hypoxic conditions. Both cell lines cultured in E8 media maintained normal karyotypes after 25 passages.
Figures 2, 4:
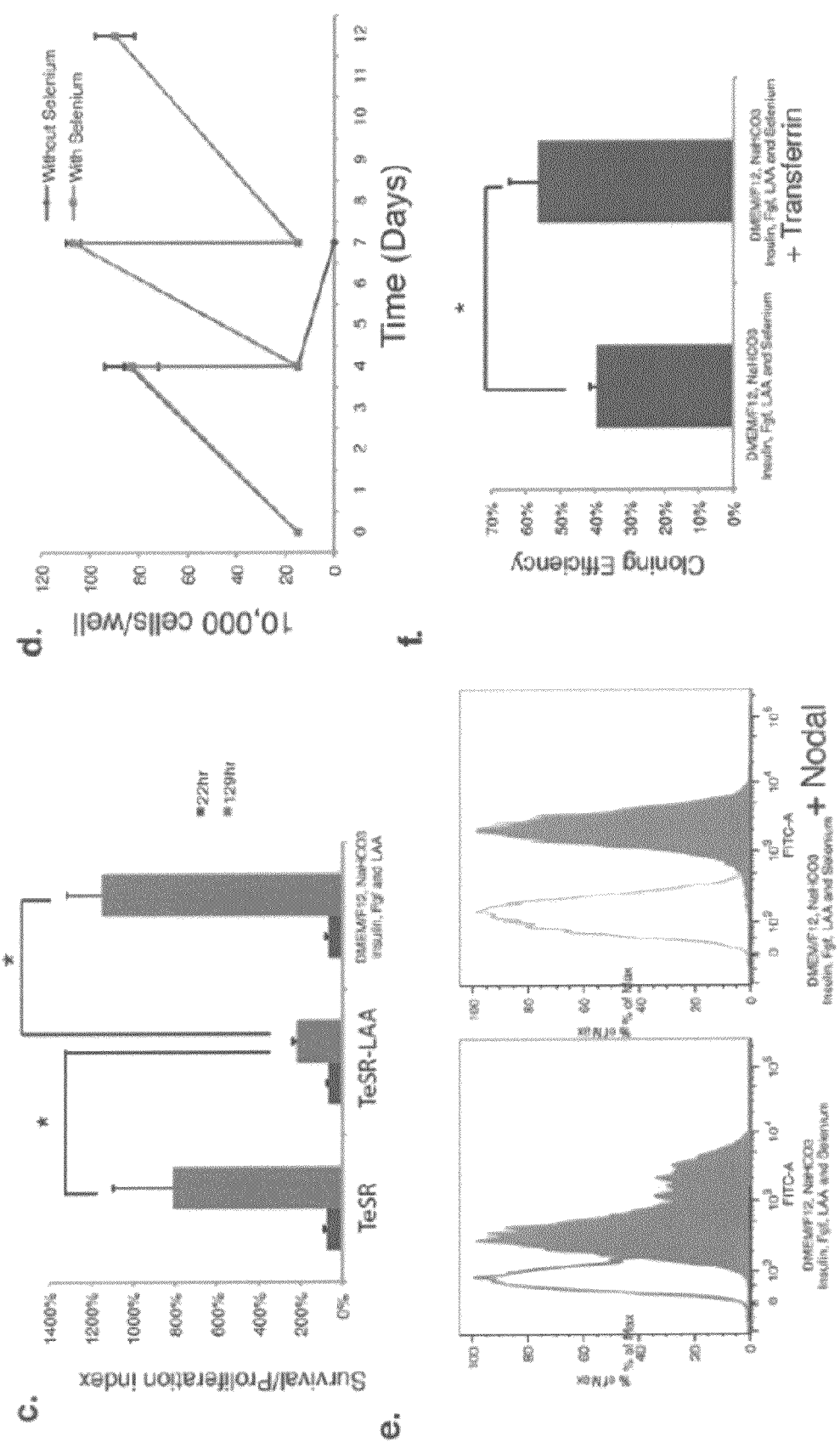
Figures 3, 4:
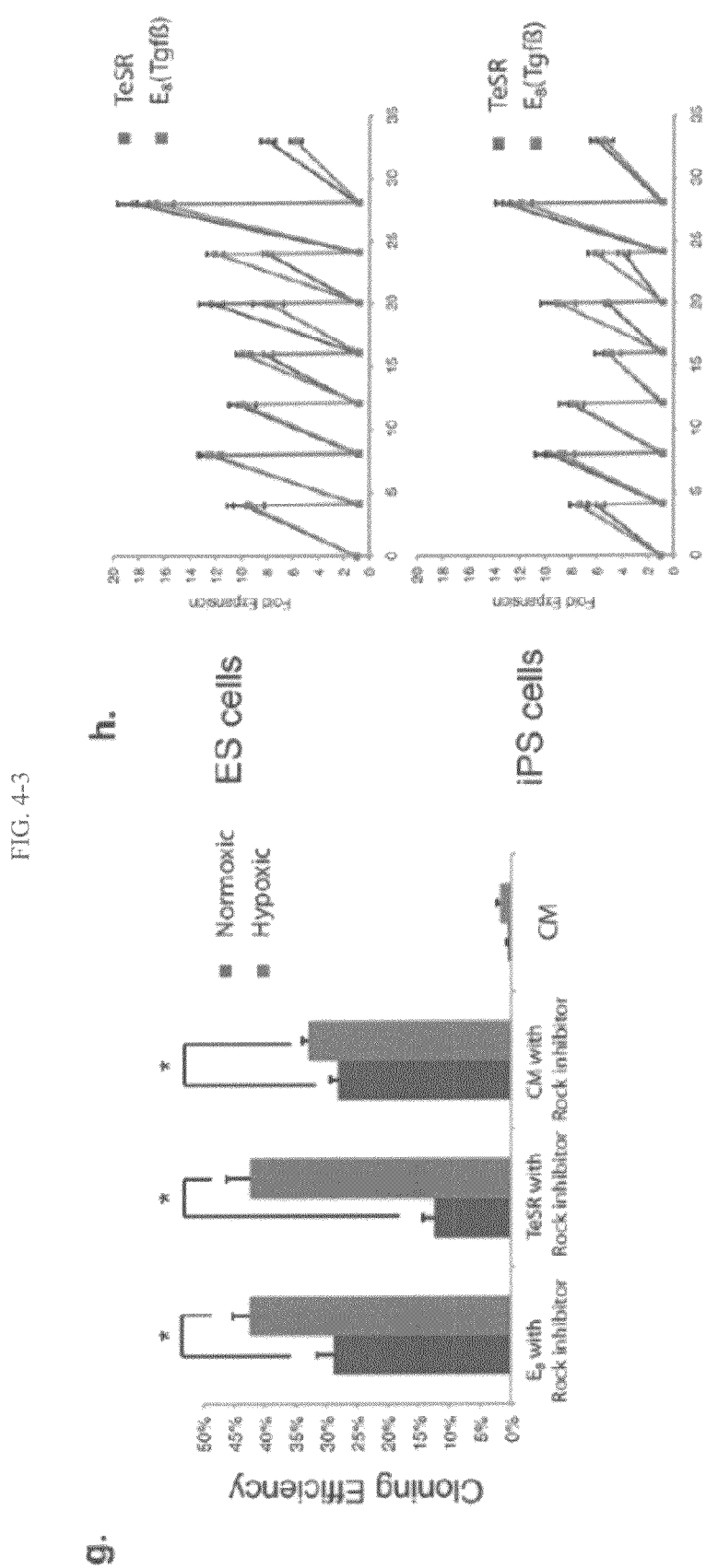
FIG. 3 illustrates the cloning efficiency of cells cultured on various matrices. Abbreviations are as in FIG. 1. Control=cells cultured on MATRIGEL™; Commercial=cells cultured on commercially available full-length vitronectin protein purified from animal cells.
Figures 1, 6:
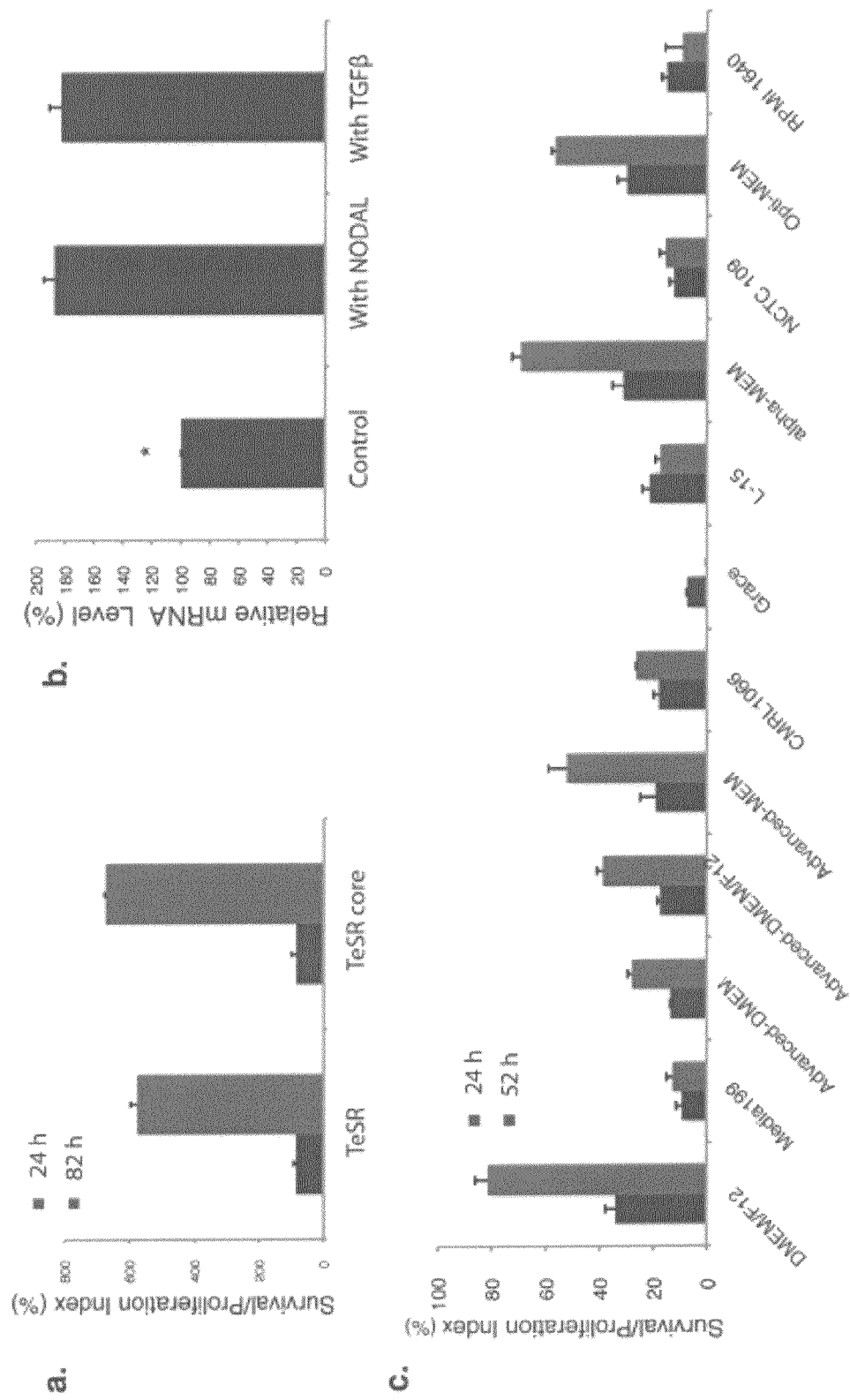
FIG. 6 illustrates media components supporting human pluripotent stem cells. (A) TGFβ, LiCl, Pipecolic acid, and GABA are not required for short-term survival and proliferation of human ES cells in TeSR. When those factors were removed, H1 ES cells survived (24 hours, blue columns) and proliferated (82 hours, red columns) as well as in TeSR. (B) Addition of NODAL (100 ng/ml) and TGFβ (2 ng/ml) in defined media (DMEM/F12, insulin, FGF2, LAA, and Selenium) maintained significantly higher NANOG expression in human ES cells (*$p<0.05$, n=3). H1 cells were maintained in specific media for 5 days (2 passages), and RNA was purified for qRT-PCR to detect NANOG expression relative to GAPDH. (C) DMEM/F12 basic media is among the best basic media in the screen that supports human ES cell survival and proliferation. A variety of basic media were used to make growth media with additional components (insulin, FGF2, LAA, Selenium, and NaHCO$_3$). Dissociated H1 cells were plated in different media on MATRIGEL-coated plates. Cell survival was measured at 24 hours (blue column) and cell proliferation at 52 hours (red column) (D) Defined media (DMEM/F12, insulin, FGF2, LAA, and Selenium) with NODAL supports pluripotency of human iPS cells. Flow cytometry detected high expression of pluripotency marker OCT4 in two iPS cell lines. Green peak: OCT4 antibody with Alexa-488 conjugated secondary antibody; Grey peak: mouse IgG control. Similar results were also obtained from H1 and H9 ES cells maintained in the same media. (E) Normal karyotypes were maintained after long-term passage for those iPS cells shown above. Normal karyotypes were also maintained in H1 and H9 ES cells cultured in the same media listed above. (F) ROCK inhibitor HA100 (10 μM) improved cell survival after dissociation in TeSR (*p<0.05, n=3). (G) HA100 also improved cloning efficiency as efficiently as Y27632 and blebbistatin in E8 media. Cells were treated with HA100 (10 μM) and Y27632) (10 μM) for 24 hours, and with blebbistatin (10 μM) for 4 hours (*p<0.05, n=3). (H) E8 (TGFβ) supported proliferation and pluripotency after long-term passage in H1 and iPS cells. High OCT4 expression was detected in H1 and iPS cells. Surface marker SSEA4 was also highly expressed. (I) Normal karyotypes were maintained after 25 passages.

In addition to the components of DMEM/F12 (Table 1), TESR™ has 18 components, the major protein component being BSA (~1% in weight). The components of TESR™ were examined in the absence of BSA and BME. Insulin and FGF2 remained important for cell survival and proliferation (FIG. 4A-B). In these conditions, we found that L-ascorbic acid (Vitamin C, LAA) promoted ES cell proliferation (FIG. 4C), and that selenium was necessary for long-term sustained growth (FIG. 4D). Comparative analysis of 12 different base media failed to identify a base medium that performed better than DMEM/F12 (FIG. 6C). It was discovered that human ES and iPS cells could be expanded in a simple medium consisting only of insulin, FGF2, L-ascorbic acid, and selenium in DMEM/F12 with pH adjusted with $NaHCO_3$, but that cultures were often prone to sporadic differentiation after long-term passage (data not shown). The addition of NODAL (100 ng $ml^{-1}$) or TGFβ (2 ng $ml^{-1}$) increased NANOG expression levels (FIG. 6B) and led to consistent long-term culture stability of both human ES and iPS cells (FIG. 4D, E). The inclusion of either a ROCK inhibitor (HA100 or Y27632) (Watanabe et al., *Nature Biotechnology* 25:681-686 (2007)) or blebbistatin (Chen et al., *Cell Stem Cell* 7:240-248 (2010)) improved initial survival and supported a high cloning efficiency (FIG. 6F, G), which was further increased by the addition of transferrin (FIG. 4F) and by culture in hypoxic conditions (FIG. 4G).

After this optimization, the final E8 medium consisted of just insulin, selenium, transferrin, L-ascorbic acid, FGF2, and TGFβ (or NODAL) in DMEM/F12 with pH adjusted with $NaHCO_3$. This simplified medium supported undifferentiated proliferation of both human ES and iPS cells comparably to TESR™ (FIG. 4H), and maintained pluripotency markers and normal karyotypes for over 25 passages and for more than three months in two ES and five iPS cell lines (FIG. 6H, I). Both ES and all five iPS cell lines tested also formed teratomas in immunocompromised mice. Global gene expression also demonstrated that cells maintained in E8 media have an expression pattern similar to cells maintained in TESR™ (data not shown).

TABLE 1

Media Components

| Components | TESR™ | TESR core | E8* |
|---|---|---|---|
| DMEM/F12 (liquid) | | | |
| L-Ascorbic Acid | | | |
| Selenium | | | |
| Transferrin | | | |
| $NaHCO_3$ | | | |
| Glutathione | | | |
| L-Glutamine | | | |
| Defined Lipids | | | |
| Thiamine | | | |
| Trace Elements B | | | |
| Trace Elements C | | | |
| β-mercaptoethanol | | | |
| Albumin (BSA) | | | |
| Insulin | | | |
| FGF2 | | | |
| TGFβ1 | | | |
| Pipecolic Acid | | | |
| LiCl | | | |
| GABA | | | |
| H2O | | | |
| NODAL | | | |
| Hydrocortisone | | | |
| Butyrate | | | |

*In E8 media, NODAL (100 ng/mL) and TGFβ (2 ng/mL) are interchangeable in maintaining ES and iPS cells. When NODAL is used, the media is specified as E8(NODAL), and likewise for TGFβ, specified as E8(TGFβ).

Example 6

Vitronectin-coated Surfaces Support ES Cell Growth in E8

Figure 5:
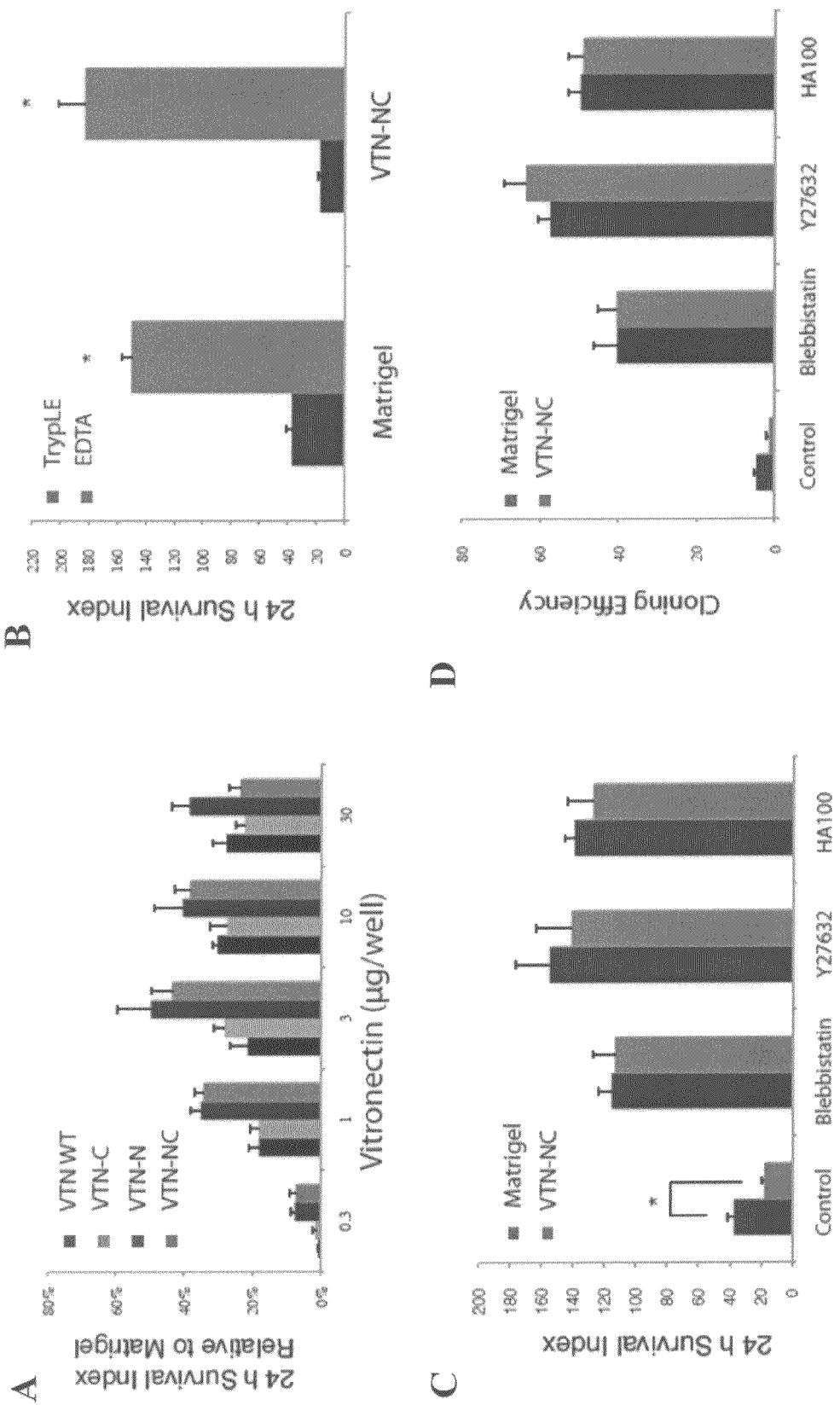
FIG. 5 demonstrates that vitronectin coated surfaces support human ES and iPS cells cultured in E8 medium. (A) Four vitronectin variants were tested by survival assay in E8 media, and the survival index was normalized with the cell survival rate on MATRIGEL™ surfaces (*$p<0.05$, n=3). (VTN-WT, black column; VTN-C, gray column; VTN-N, blue column; and VTN-NC, red column) (B) VTN-NC (red column) and MATRIGEL™ (blue column) surfaces were compared in survival assay in E8(TGFβ) media with different passaging methods, EDTA (red column) and TrypLE (blue column) (*$p<0.05$, n=3). (C) VTN-NC and MATRIGEL™ surfaces were compared in survival assay in E8 (TGFβ) media with either Blebbistatin or ROCK inhibitors (10 μM Blebbistatin, 10 μM Y27632, or 10 μM HA100) (*$p<0.05$, n=3). (D) VTN-NC (red column) and MATRIGEL™ (blue column) surfaces were compared in cloning assay in E8 (TGFβ) media with drug treatments (Blebbistatin, Y27632, or HA100) (*$p<0.05$, n=3).

Multiple matrix proteins such as laminin, vitronectin, and fibronectin support human ES cell growth. Synthetic surfaces have also been developed for human ES cells. Most of these materials are too expensive for large-scale use. Because vitronectin is relatively easy to overexpress and purify (see Braam et al., *Stem Cells* 26:2257-2265 (2008)), assays were performed to identify vitronectin polypeptide variants that support human ES cell attachment and survival better than wild type vitronectin when cultured in E8 medium. Two such vitronectin polypeptide variants (VTN-NC and VTN-N) were identified (FIG. 5A). VTN-NC was used for further studies. VTN-NC supported initial attachment and survival of human ES cells well in E8 medium when cells were passaged in small clumps using EDTA, but less efficiently than MATRIGEL™ when cells were passaged as single cells (FIG. 5B). When a ROCK inhibitor (HA100 or Y27632) or blebbistatin was added, VTN-NC supported both initial human ESC survival and cloning efficiency as effectively as MATRIGEL™ (FIG. 5C, D).

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for maintaining pluripotent stem cells in culture, the method comprising culturing pluripotent stem cells on a substrate comprising one or both of the polypeptides selected from the group consisting of residues 43 to 378 of SEQ ID NO: 1 and residues 45 to 378 of SEQ ID NO: 1, whereby the substrate maintains the cultured pluripotent stem cells as a substantially undifferentiated cell population for at least 20 passages.

2. The method of claim 1, wherein the pluripotent stem cells are cultured under fully-defined conditions.

3. The method of claim 2, wherein the pluripotent stem cells are cultured in a defined culture medium comprising insulin, selenium, transferrin, L-ascorbic acid, FGF2, DMEM/F12, NaHCO$_3$, and one of TGFβ and NODAL.

4. The method of claim 2, wherein the pluripotent stem cells are cultured in a defined culture medium consisting essentially of insulin, selenium, transferrin, L-ascorbic acid, FGF2, DMEM/F12, NaHCO$_3$, and one of TGFβ and NODAL.

5. The method of claim 1, wherein the substrate is substantially free of xenogenic contamination with regard to the pluripotent stem cells.

6. A method for cloning a pluripotent cell, the method comprising plating iPS cells at cloning density in a defined culture medium on a substrate comprising one or both of the polypeptides selected from the group consisting of residues 43 to 378 and residues 45 to 378 of SEQ ID NO: 1.

7. The method of claim 6, wherein the defined medium comprises insulin, selenium, transferrin, L-ascorbic acid, FGF2, DMEM/F12, NaHCO$_3$, and one of TGFβ and NODAL.

8. The method of claim 6, wherein the defined medium consists essentially of insulin, selenium, transferrin, L-ascorbic acid, FGF2, DMEM/F12, NaHCO$_3$, and one of TGFβ and NODAL.

9. The method of claim 1, wherein the substrate maintains the pluripotent stem cells substantially free from differentiation for at least 25 passages.

10. The method of claim 1, wherein the pluripotent stem cell is an induced pluripotent stem (iPS) cell.

11. The method of claim 10, wherein the iPS cell is obtained by reprogramming a somatic cell to pluripotency.

12. The method of claim 11, wherein the somatic cell is reprogrammed on the substrate.

13. The method of claim 11, wherein the somatic cell is reprogrammed in the presence of a defined culture medium.

14. The method of claim 13, wherein the defined culture medium comprises insulin, selenium, transferrin, L-ascorbic acid, FGF2, DMEM/F12, NaHCO$_3$, and one of TGFβ and NODAL.

15. The method of claim 13, wherein the defined medium consists essentially of insulin, selenium, transferrin, L-ascorbic acid, FGF2, DMEM/F12, NaHCO$_3$, and one of TGFβ and NODAL.

* * * * *